United States Patent [19]
Sapkos

[11] Patent Number: 5,816,809
[45] Date of Patent: Oct. 6, 1998

[54] DENTAL PROSTHESIS SUPPORT DEVICE AND METHOD OF USING SAME

[75] Inventor: Stanley W. Sapkos, Seattle, Wash.

[73] Assignee: Genetic Implant Systems, Inc., Seattle, Wash.

[21] Appl. No.: 707,416

[22] Filed: Sep. 4, 1996

Related U.S. Application Data

[60] Provisional application No. 60/004,026 Sep. 20, 1995.

[51] Int. Cl.$^6$ .................................................... A61C 8/00
[52] U.S. Cl. ............................................ 433/172; 433/173
[58] Field of Search ................................... 433/172, 173, 433/174, 175, 176

[56] References Cited

U.S. PATENT DOCUMENTS

| Re. 33,796 | 1/1992 | Niznick | 433/173 |
|---|---|---|---|
| 711,324 | 10/1902 | Lacy | 433/174 |
| 866,304 | 9/1907 | Roach . | |
| 2,112,007 | 3/1938 | Adams | 32/2 |
| 2,347,567 | 4/1944 | Kresse | 32/12 |
| 2,609,604 | 9/1952 | Sprague | 32/1 |
| 2,909,055 | 10/1959 | Fish | 73/1 |
| 3,255,624 | 6/1966 | Larson | 73/1 |
| 3,435,526 | 4/1969 | Brancato | 32/10 |
| 3,456,485 | 7/1969 | Larson | 73/1 |
| 3,498,103 | 3/1970 | Larson | 73/1 |
| 3,499,222 | 3/1970 | Linkow et al. | 32/2 |
| 3,732,621 | 5/1973 | Bostrom | 32/10 A |
| 4,016,651 | 4/1977 | Kawahara et al. | 32/10 A |
| 4,051,559 | 10/1977 | Pifferi | 3/1.912 |
| 4,109,383 | 8/1978 | Reed et al. | 32/10 A |
| 4,177,562 | 12/1979 | Miller et al. | 433/174 |
| 4,180,910 | 1/1980 | Straumann et al. | 433/173 |
| 4,187,609 | 2/1980 | Edelman | 433/176 |
| 4,259,072 | 3/1981 | Hirabayashi et al. | 433/173 |
| 4,324,550 | 4/1982 | Reuther et al. | 433/174 |
| 4,359,318 | 11/1982 | Gittleman | 433/173 |
| 4,416,629 | 11/1983 | Mozsary et al. | 433/174 |

(List continued on next page.)

FOREIGN PATENT DOCUMENTS

| 0 000 549 | 2/1979 | European Pat. Off. . |
|---|---|---|
| 0 073 177 | 3/1983 | European Pat. Off. . |
| 30 27 138 | 12/1981 | Germany . |
| 540 713 | 3/1956 | Italy . |
| 51-117493 | 10/1976 | Japan . |
| 52-12797 | 1/1977 | Japan . |
| 61-41580 | 9/1986 | Japan . |
| 3-210447 | 9/1991 | Japan . |
| 413 224 | 5/1966 | Switzerland . |
| 1654693 | 6/1991 | U.S.S.R. . |
| 1 203 093 | 8/1970 | United Kingdom . |
| 1 291 470 | 10/1972 | United Kingdom . |
| 1 352 188 | 5/1974 | United Kingdom . |
| 1 544 784 | 4/1979 | United Kingdom . |
| WO 83/02555 | 8/1983 | WIPO . |

OTHER PUBLICATIONS

Lekholm, "Clinical procedures for treatment with osseointegrated dental implants", *The Journal of Prosthetic Dentistry*, vol. 50, No. 1, Jul. 1983, pp. 10A, 118.

Niznick, "Implant Prosthodontics, A Team Approach", *Journal of Oral Implantology*, vol. XII, No. 1, 1985, pp. 1, 6, 12, 57, 68.

Zest Anchor, advertisement of Zest Anchors, Inc., San Diego California.

*Primary Examiner*—John J. Wilson
*Attorney, Agent, or Firm*—Sheridan Ross P.C.

[57] ABSTRACT

A support device or post for fitting into an implant implanted into a patient which is configured to support a dental prosthesis is provided. An upper portion of the post, in one embodiment, has external screw threads for coupling a healing cap. The upper portion of the post may be removed or broken away at a weakened portion or constriction. The support device has a collar which can define various heights or diameters. The support device can be positioned in the implant by mating screw threads with the support device being torqued to a predetermined torque, preferably using a torque wrench which can be set using a non-variable, preferably gravity-based, standard.

19 Claims, 5 Drawing Sheets

U.S. PATENT DOCUMENTS

| | | | |
|---|---|---|---|
| 4,431,416 | 2/1984 | Niznick | 433/174 |
| 4,468,200 | 8/1984 | Münch | 433/174 |
| 4,488,875 | 12/1984 | Niznick | 433/173 |
| 4,531,915 | 7/1985 | Tatum, Jr. | 433/173 |
| 4,541,313 | 9/1985 | Wise | 81/478 |
| 4,552,532 | 11/1985 | Mozsary | 433/173 |
| 4,624,673 | 11/1986 | Meyer | 623/16 |
| 4,626,214 | 12/1986 | Artal | 433/174 |
| 4,645,453 | 2/1987 | Niznick | 433/173 |
| 4,661,066 | 4/1987 | Linkow et al. | 433/176 |
| 4,668,191 | 5/1987 | Plischka | 433/174 |
| 4,713,003 | 12/1987 | Symington et al. | 433/173 |
| 4,713,004 | 12/1987 | Linkow et al. | 433/174 |
| 4,744,754 | 5/1988 | Ross | 433/173 |
| 4,758,161 | 7/1988 | Niznick | 433/173 |
| 4,761,989 | 8/1988 | McDevitt | 73/1 C |
| 4,772,204 | 9/1988 | Söderberg | 433/174 |
| 4,826,434 | 5/1989 | Krueger | 433/174 |
| 4,960,381 | 10/1990 | Niznick | 433/174 |
| 4,976,133 | 12/1990 | Pohl | 73/1 C |
| 4,976,739 | 12/1990 | Duthie, Jr. | 433/174 |
| 5,030,095 | 7/1991 | Niznick | 433/173 |
| 5,061,181 | 10/1991 | Niznick | 433/174 |
| 5,062,800 | 11/1991 | Niznick | 433/229 |
| 5,071,350 | 12/1991 | Niznick | 433/173 |
| 5,073,111 | 12/1991 | Daftary | 433/173 |
| 5,076,788 | 12/1991 | Niznick | 433/173 |
| 5,078,607 | 1/1992 | Niznick | 433/174 |
| 5,145,372 | 9/1992 | Daftary et al. | 433/173 |
| 5,181,425 | 1/1993 | Livingston | 73/862.08 |
| 5,281,140 | 1/1994 | Niznick | 433/172 |
| 5,295,831 | 3/1994 | Patterson et al. | 433/141 |
| 5,334,024 | 8/1994 | Niznick | 433/173 |
| 5,337,638 | 8/1994 | Coss et al. | 81/483 |
| 5,350,297 | 9/1994 | Cohen | 433/173 |
| 5,417,568 | 5/1995 | Giglio | 433/173 |
| 5,622,499 | 4/1997 | Simmons | 433/172 |

DENTAL PROSTHESIS SUPPORT DEVICE AND METHOD OF USING SAME

This application claims the benefit of U.S. Provisional application Ser. No. 60/004,026, filed Sep. 20, 1992.

The present invention relates to a novel support device and system for use in fabricating and supporting dental prosthesis, and a novel method of installing the same into a patient, utilizing a previously implanted hollow implant device.

BACKGROUND INFORMATION

Implant systems consisting of an implant or root portion embedded in a patient's bone or tissue and a post or support device for receiving a prosthesis are widely used. They are used most often in implanting permanent teeth or crowns into the jawbones and surrounding tissue of patients.

Existing devices and methods often result in an incorrect fit of the prosthesis with the anchoring device and surrounding tissue. Another problem with certain previous systems was the inability to fabricate a closely fitting permanent prosthesis without time-consuming and unwieldy procedures such as removing and reassembling the components of the implant and post or fabricating a permanent prosthesis by taking laborious and often inaccurate measurements of a temporary cap after the implant, post and temporary cap had been installed in the patient.

Yet another problem in some implant devices was the tendency for the gum tissue (gingiva) to grow inward over the top of the implant before installation of the permanent prosthesis, so that the tissue had to be cut away from the top of the implant before a prosthesis could be secured to the implant or post, thus resulting in trauma to the patient and ultimately a poor fit between the implant, post and prosthesis. The poor fit also resulted in food particles becoming wedged between the prosthesis and the cap or implant, leading to decay.

Another problem with certain previous implants was the inability to keep a support post firmly anchored in a receiving device already implanted in the patient's bone without cross-threading or stripping either or both of the support post and receiving device.

Another problem with installing certain previous implant devices was the difficulty associated with calibrating and applying a correct amount of torque to the post so as to attach it firmly to the implant device, e.g., without rotating the implant device, and thus damaging or traumatizing the patient and surrounding bone and tissue.

Certain previous torque wrenches for use with dental implant devices depended on the user noticing when slippage of the wrench occurred against the prosthesis or post. Some previous torque wrenches had a linear scale along their body to indicate the torque value set, which was hard to read. In spring-based wrenches the torque indication became inaccurate as the spring constant of varied with use and/or metal fatigue. Utilizing other wrenches depended on the user's skill in noticing changes in the connection between the wrench and the implant or post. This resulted in stripping the screw threads inside the implant when the practitioner's judgment was flawed, or rotating the implant and causing patient trauma. In some designs, the wrench deformed when a predetermined torque was reached.

Many previous methods of calibrating a wrench to a specific torque relied upon a variable, spring-based standard. This method had at least two drawbacks: first, the torque amount varied as the spring experienced metal fatigue and/or eventual change in the spring constant, and second, the torque wrench typically could only be set infrequently. Many previous calibration devices for torque wrenches relied on complex machinery to calibrate a measuring device which in turn was itself used to calibrate a torque wrench, or alternatively relied on magnets to calibrate torque.

Accordingly, it would be advantageous to provide a device for implanting and securing prostheses which results in a precise degree of fit between the support device and the implant, the support device and the surrounding tissue, and the support device and the prosthesis. It would be advantageous to provide a method for installing the support device utilizing a non-spring based torque setting for a torque wrench for inserting the support device into the implant. It would also be advantageous to provide a device for fabricating a permanent prosthesis whose shape closely reproduced the support device for the prosthesis, so as to eliminate tedious measurements of the prosthesis in the patient's mouth, and provided for a more precise fit between the prosthesis and the support device.

SUMMARY OF THE INVENTION

A novel and useful invention relates to fabricating and/or installing a prosthesis into patients. The prosthesis is usually a temporary healing cap or permanent dental crown. A hollow receiving device or "implant" is implanted into a patient, usually into the patient's jaw bone (alveolar). A support device or "post" is fitted into the implant and extends upwardly away from the jaw bone for receiving a healing cap and/or a permanent prosthesis.

In one embodiment, the support device has three portions, a distal root portion, a middle collar portion and an upper post portion. The distal root portion may additionally have external screw threads located above a smooth lower surface. The distal root portion extends into the implanted receiving device and is initially fitted into the receiving device by manually inserting the smooth end into the implanted receiving device. The smooth end functions as a lead so that the support device initially fits loosely in the implanted receiving device but is substantially axially aligned (e.g., to avoid cross-threading), awaiting tightening to a predetermined torque setting.

In one embodiment, various sizes of the middle collar portion are provided to accommodate different tissue thicknesses and/or prosthesis size.

In one embodiment, the top of the support portion of the post has a breakaway feature effected by a weakened (e.g., lesser diameter) section. In yet another embodiment, the topmost portion of the post has external threads which allow connection with a temporary healing cap. The healing cap may then be broken off prior to installation of the permanent prosthesis without damage to the rest of the post, implant, bone or tissue. Alternatively, the permanent prosthesis may be seated directly on the healing cap.

In one embodiment of the invention, the uppermost portion of the post is tapered to provide a secure fit with the prosthesis and lessen the possibility of splintering of the prosthesis.

In one embodiment, the external surface of the upper part of the support device has a hexagonal wrench-engaging surface. The surface may be used to fit the post into the implant with a torque wrench. The surface may be used by the practitioner to index the prosthesis to the post.

Another feature of the invention is the use of a replica of the post as a mold or analogue to fabricate a temporary healing cap or permanent prosthesis. This feature allows fabrication without dissembling and reassembling the post and/or implant from the patient's mouth and increases the degree of fit and compatibility between the prosthesis and post.

One embodiment of the invention utilizes a non-spring based torque wrench to install the support member. The wrench is set at a predetermined torque level using a non-spring, non-variable, weight-based calibration device and results in installation of the support device without rotation of the implant or damage to the surrounding tissue or bone.

DETAILED DESCRIPTION OF THE PREFERRED EMBODIMENTS

Figure 1:
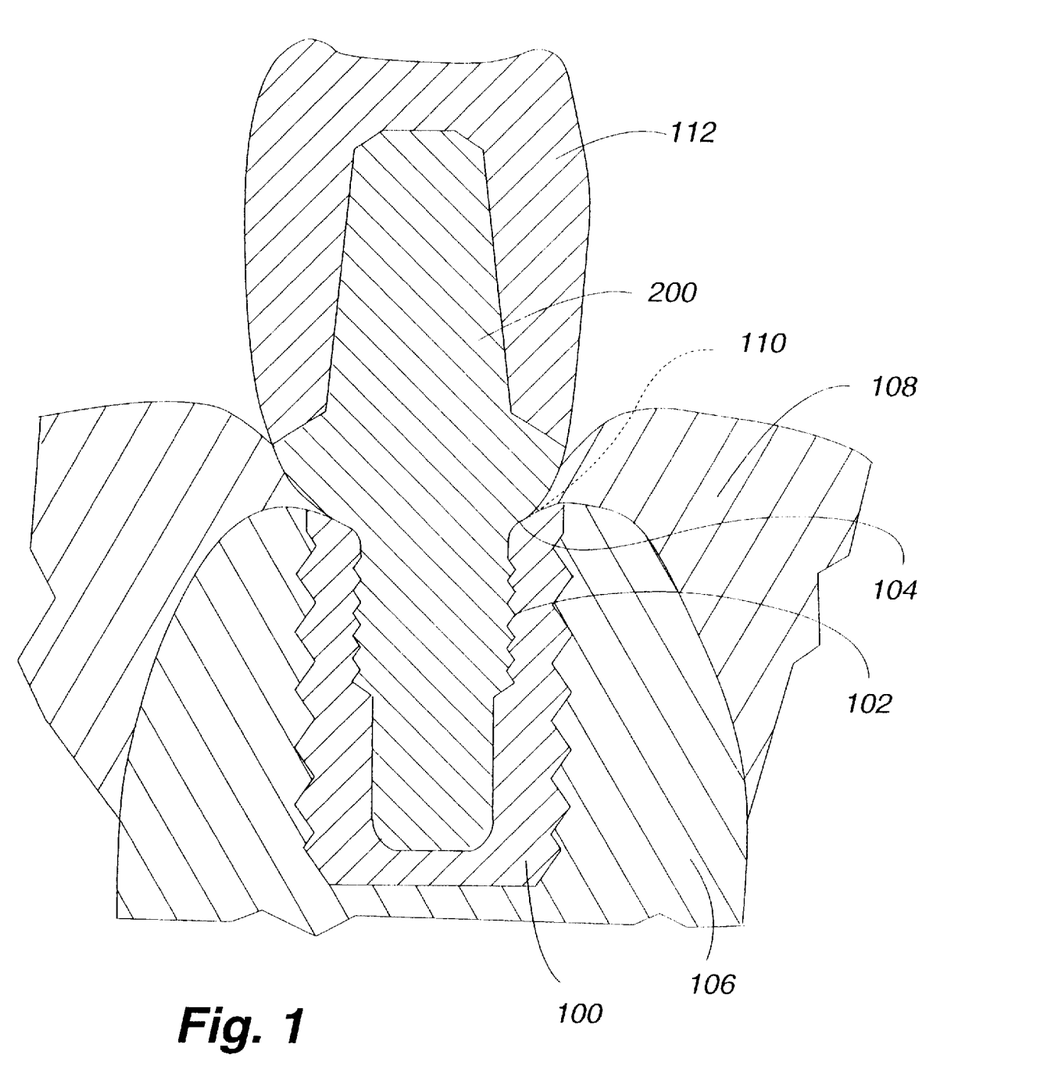
FIG. 1 is a cross-sectional view of an implant, post, and prosthesis coupled to a jaw bone according to one embodiment of the present invention.

The invention relates to a dental prosthesis device and method for installing same into a hollow implant 100 as shown in FIG. 1 which has already been embedded in the patients bone 106. The implant device may have internal screw threads 102 and an interior upper surface 104. The upper surface may be beveled, or smooth, flat and/or may have an external or internal slot or other shape for engagement by a driver such as a slot or Philip's screwdriver, a hex or other wrench or the like. The implant 100 may be anchored in the bone 106 by screw threads, by a press or interference fit and the like. A number of implants can be used including those available from Genetic Implant Systems, Inc. of Seattle, Wash.

Figure 2:
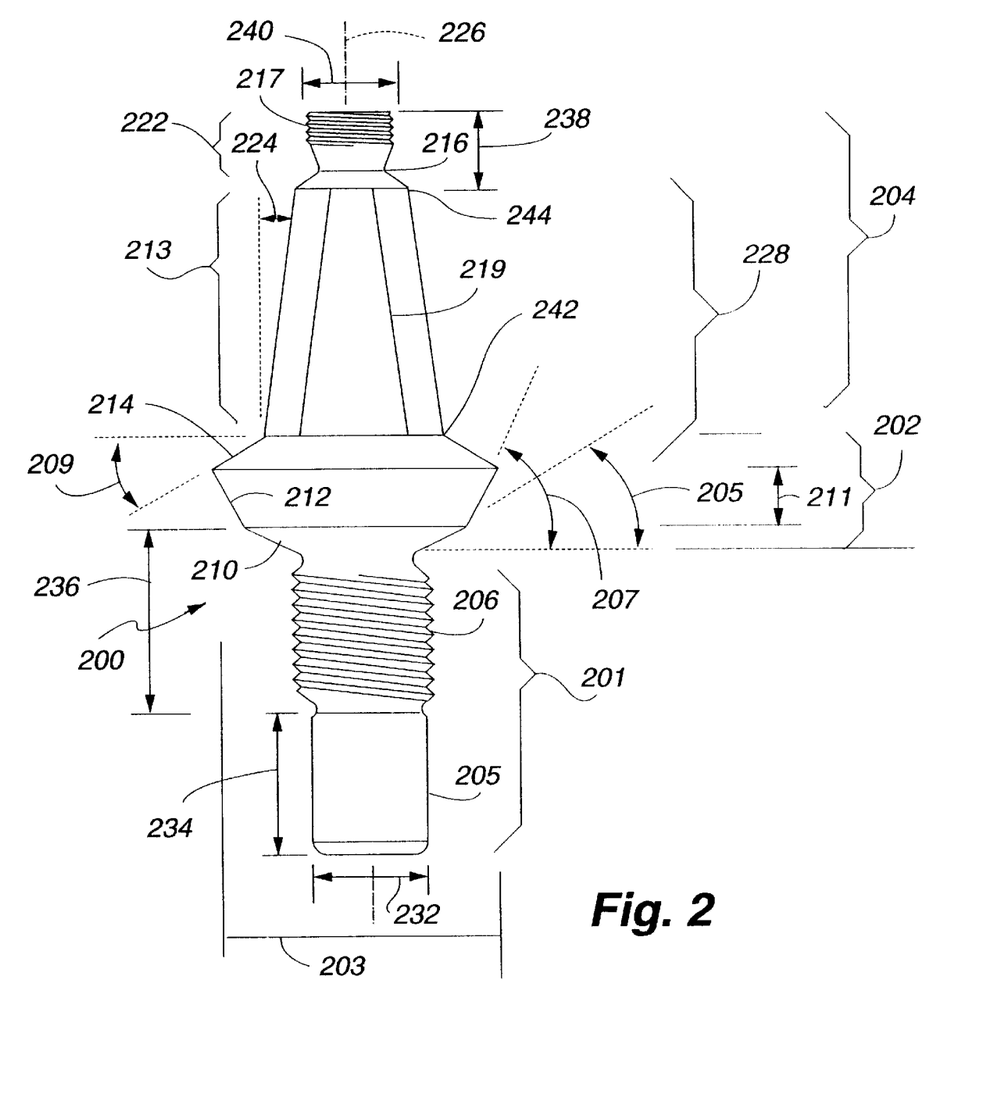
FIG. 2 is an elevational view of a support structure according to an embodiment of the present invention.

As shown in FIG. 2, a support device or "post" has three portions, a distal root portion 200, a middle collar portion 202 and an upper post portion 204. The distal root portion is roughly cylindrical in shape and may have external screw threads 206 located above a smooth lower surface 208. Although the extent of the lower root portion of the post which is threaded can be varied, in one embodiment at least about 3.5 mm of the post is threaded. A number of materials can be used for making the support device. Including stainless steel, surgical steel, titanium or titanium allow which may be coated with an HA coating. Other materials that can be used include composites such as fiber reinforced resins, ceramics, and the like.

In one embodiment, the middle collar portion 202 of the post defines a surface of revolution (although other shapes may be used such as elliptical or hexagonal in cross section) and has an outward flaring flange, of greater size (e.g., diameter 203) than either the lower 200 or upper 204 portions of the post. In the depicted embodiment, the flange defines three angled surfaces, which are, from most distal to most proximal, 210, 212 and 214 respectively. The lowermost or most distal portion of the flange 210 flares outward at a smaller angle 205 relative to the horizontal than the angle 207 of flange surface 212. The angle 205 is selected to provide a good seal with a surface of the implant 100, such as being about equal to or slightly less than the angle of bevel 104. The first and/or second surfaces 210, 212 may be provided with one or more recesses, e.g., to accommodate an implant protuberance, such as a driving surface. Angle 207 is determined by the desired diameter 203 and collar height 211. Preferably many posts with different diameters 203 and collar heights are available for the dentist to select among, e.g., to suit the tooth/jaw size and gum thickness of the patient. The uppermost or most proximal flange surface 214 slopes inward to the upper portion of the post 204, preferably at an angle 209 of between about 0° and about 60°, more preferably, about 30°.

The upper portion 204 of the post may include a tapered region 213. In one embodiment, the taper of the tapered portion of the post is between about 2 and 12 degrees. Without wishing to be bound by any theory, it is believed that if the tapered portion is too sharply tapered, there can be a retention problem. Providing that at least some taper is believed to be useful with drawing, fastening, crowns, and in situations in which crowns are splinted together. In one embodiment, the upper portion of the post has a weakened portion 216, e.g., a region of lesser diameter than adjacent portions of the post. In the depicted embodiment, an externally threaded region 217 is separated from the tapered portion 213 by the constriction 216. The post may additionally have a wrench-engaging external surface, such as a flat surface. In the depicted embodiment, the tapered region 213 is hexagonal in cross-section, to define six flat faces, e.g., for engaging a hex-wrench.

The distal root portion of the support device or post 200 is initially fitted into the implant 100 by manually inserting the smooth end 208 into the threaded well of the implant. The smooth end 208 functions as a lead so that the support device initially fits loosely in the implant awaiting tightening to a predetermined torque setting, but is sufficiently axially aligned with the implant to substantially avoid crossthreading between screw threads 206 of the post and 102 of the implant.

The support device or post is then tightened to a predetermined torque setting, e.g., by using the torque wrench 500 described below engaged with the hexagonal outer surface 219 of the upper portion 204 of post 200. Insertion of the post 200 into the implant 100 by this method substantially avoids rotation of the implant 100, cross-threading or stripping of the internal screw threads 102 and trauma to the patient's bone and surrounding tissue. Beveled surface 104 of the implant additionally provides a closely fitting match with surface 210 of the support device.

In one embodiment, angle 205 is slightly less (such as about 1° less) than the angle of the implant bevel 104. The post 200 and/or implant 100 have sufficient resilience and/or ductility that the torqued screw-engagement of the post 200 and implant pull the post 200 sufficiently tight against the upper surface 104 of the implant that the post and implant are effectively in a sealing relation, substantially preventing entry of bacteria and/or tissue encroachment between the post 200 and implant 100. In one embodiment, the angle 209 is about 30 degrees. It is believed that providing at least some angle or bevel to surface 214 is useful in order to make it easier to seat the prosthesis or crown.

After insertion of the support device or post 200 into implant 100, the middle collar portion 202 defines an emergence profile 110 between the post 200 and the surrounding tissue 106 at 110. The emergence surface starts at the top of the implant 100. The middle collar portion's position, surface and/or shape inhibit the growth of the surrounding tissue 108 into and over the top of the implant 100. The middle collar portion 202 may additionally have a variety of widths and thicknesses to accommodate varying tissue thickness and prosthesis shape and size.

The upper flange surface 214 provides a close fit with the internal base of permanent prosthesis 112, thus diminishing the possibility of creating an area between the prosthesis and post susceptible to food particle invasion, bacterial infection and decay.

A temporary healing cap 300 (FIG. 3) with internal screw threads 302 is fitted over post 200 by mating with the external threads 217 of post 200. If desired, a temporary tooth prosthesis may be fabricated or attached to one extended surface 306 of one cap, e.g., for providing a more pleasing appearance during healing. Threading the temporary healing cap obviates the need for cementation of the temporary healing cap to the post with its attendant risk of infection and irritation. Lower surface 304 of the temporary healing cap is positioned adjacent to surface 214 of the middle collar portion 202 of post 200, also inhibiting overgrowth of the surrounding tissue 108. Although, in the depicted embodiment, the healing cap would have a lower rim which was positioned at or above the gum line, if desired, the lower rim of the healing cap could extend somewhat below the gum line. Although a number of materials can be used for fabricating the healing cap, in one embodiment, the cap is fabricated from or includes acrylic. In one embodiment, both the post and the implant are comprised of titanium.

Figure 3:
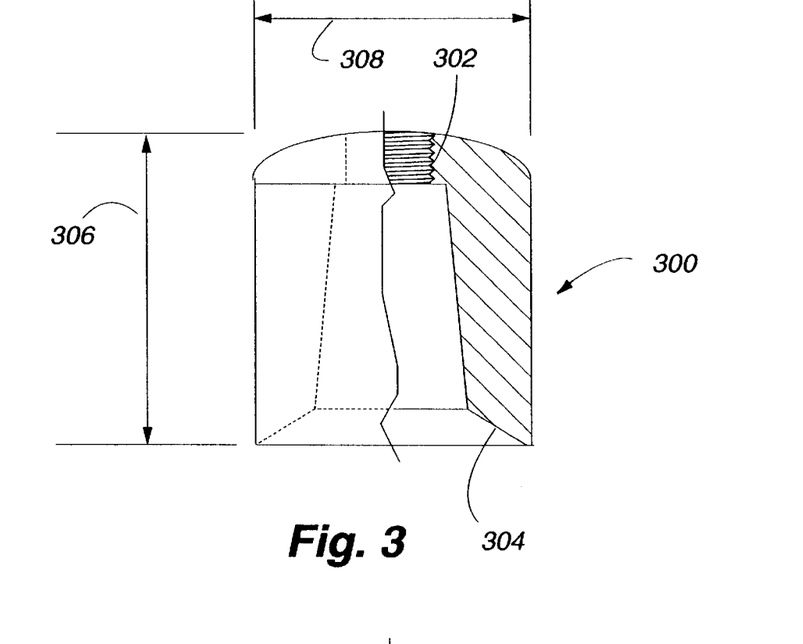
FIG. 3 is a cross-sectional view of a healing cap according to an embodiment of the present invention.

The temporary healing cap 300 may be removed by unscrewing, thus making it possible to easily remove and, if desired, re-install the healing cap. The tip 222 of the post 200 may be removed, e.g. prior to installing the permanent prosthesis, by applying pressure to the top, thus causing breakage of the post top 222 at the weakened area 216. The tip may also be removed by a wire cutter. Alternatively, permanent prosthesis 112 may be cemented to the post 200 without removing the tip 222.

A permanent prosthesis or crown 112 may be affixed to the upper portion of the post 204, e.g. as depicted in FIG. 1. The external surface 219 of the upper portion of the post 204 serves to seat and fit the permanent prosthesis snugly on the post, and allows the practitioner to index the permanent prosthesis to the post. The angle of taper 224 of the tapered portion 213 is selected to provide sufficient holding or cementation surface while accommodating minor post misalignment, e.g. in the case of multiple splinted or coupled tooth prostheses. The angle 224 is preferably less than about 10 degrees and is more preferably about six degrees.

Figure 4:
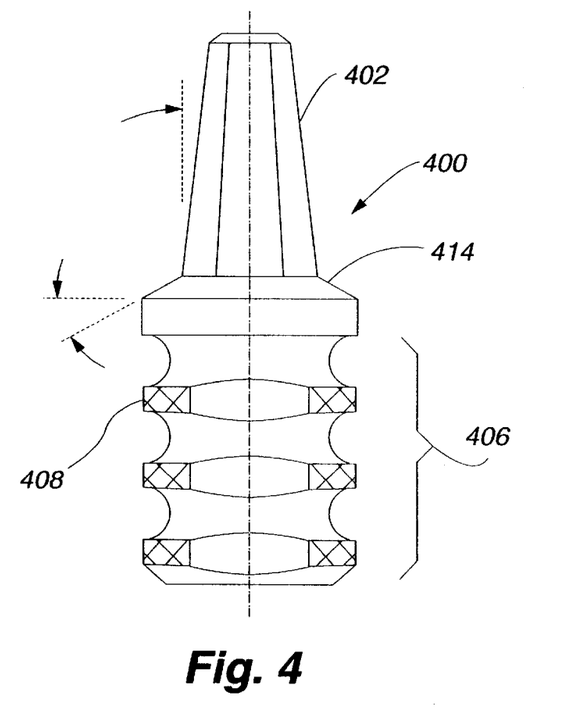
FIG. 4 is an elevational view of an analog device according to an embodiment of the present invention.

Referring to FIG. 4, another aspect of the invention involves a replica or analogue 400 of the upper portion 228 of post 204 e.g. for use in fabricating a permanent prosthesis 112. The analogue 400 may have a hexagonal outer surface 402 to match the external surface 217 and upper flange surface 414 defining an angle and diameter similar to the angle 209 and diameter 203 of the installed post 200. While the tissue and bone are healing after positioning the implant 100, the practitioner will take an impression from the patient's mouth. The practitioner may then make a mold from the impression and insert the analogue 400 into the mold.

The practitioner can then use the combination of the analogue 400 and its relation to surrounding teeth and tissue as indicated by the mold to fashion a permanent prosthesis 112 which will comfortably fit into the patient and will have a recess having a shape exactly matching the shape of the upper portion 228 of the installed post. The fabrication is done without the need to dissemble and reassemble the post from the implant and also minimizes the need to reshape the prosthesis e.g because of failure to initially fit into the patient.

Figure 5:
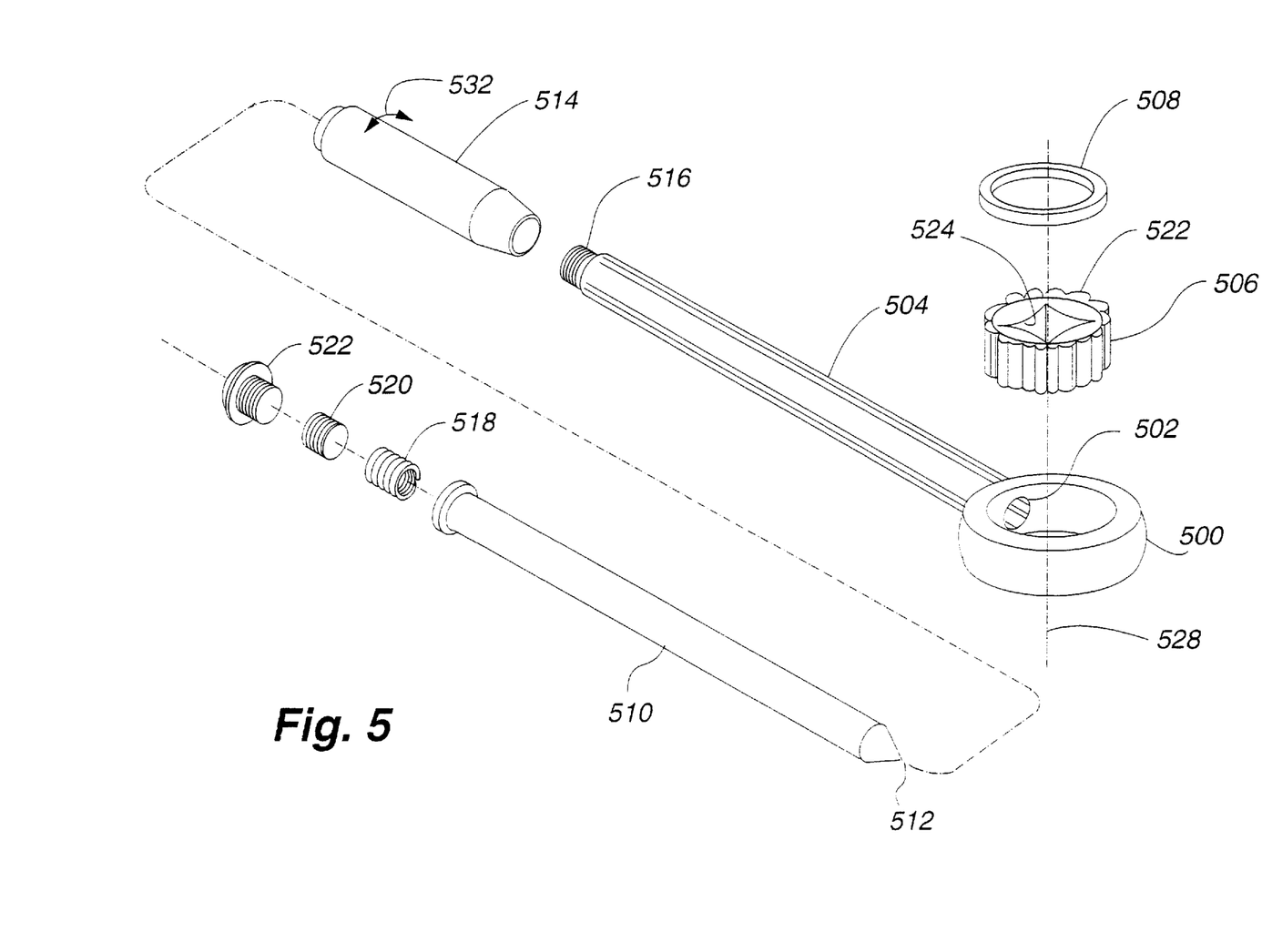
FIG. 5 is a prospective exploded view of a torque wrench according to an embodiment of the present invention.

Referring to FIG. 5, a torque wrench has an annular head 500 with an opening 502 into which is fitted a hollow shaft 504. An adjustable ratchet head 506 fits into head and is secured in the head by a retaining ring 508. Ratchet head 506 has a square opening 524 for engaging a square drive of a hexagonal socket (not shown) configured to engage the post 200. A plunger 510 tapered at one end 512 is inserted into shaft 504 so that end 512 contacts the external teeth 522 of ratchet head 506. The upper end of plunger 510 is fitted into the lower portion of a hollow handle 514. The hollow handle 514 may be attached to shank 504 by a threaded surface 516. A spring 518 held in place by a set screw 520 is inserted into handle 514 above plunger 510 covered by attaching cap 522. The plunger 510 is urged by the spring 518 towards the ratchet head 506 so that the pointed end 512 engages between teeth 522 of the ratchet head. This engagement resists rotation of the ratchet head 506 with respect to the annular head 500 about the torque axis 528 so that rotation of the shaft 504 about axis 528 causes rotation of the ratchet head 506 (and, thus, of any attached socket). This resistance to rotation of the ratchet 506 with respect to the annular head 500 can be overcome. If there is sufficient torque being transferred from the ratched head 506 to the driven object (e.g. because the driven object is relatively well-seated, or otherwise resists further rotation), attempts to rotate the annular head 500 with a greater torque will cause the point 512 to ride or cam up the side of a tooth 522, compressing plunger 510 against the urging of the spring 518 and causing relative rotation or slipping of the ratchet 506 with respect to the annular head 500. Thus, the maximum amount of torque that can be transferred from the wrench to the driven object, before slipping occurs, depends on the amount of spring force, and thus the amount of compression of the spring 518. This amount of spring force (and thus the maximum torque developed by the wrench) can be adjusted by rotating the handle 514 in direction 532 to adjust the amount of spring compression.

Although it would be possible to mount a scale on the shaft 504 bearing indicia of the amount of torque, such a scale is believed to be unreliable for may applications because the amount of spring force developed by the spring 518 will change through time because of metal fatigue or other aging effects. For this reason, according to one embodiment of the invention, a separate calibration device is provided for setting the torque of the wrench, preferably using a non-variable standard, such as the force of gravity.

Figure 6:
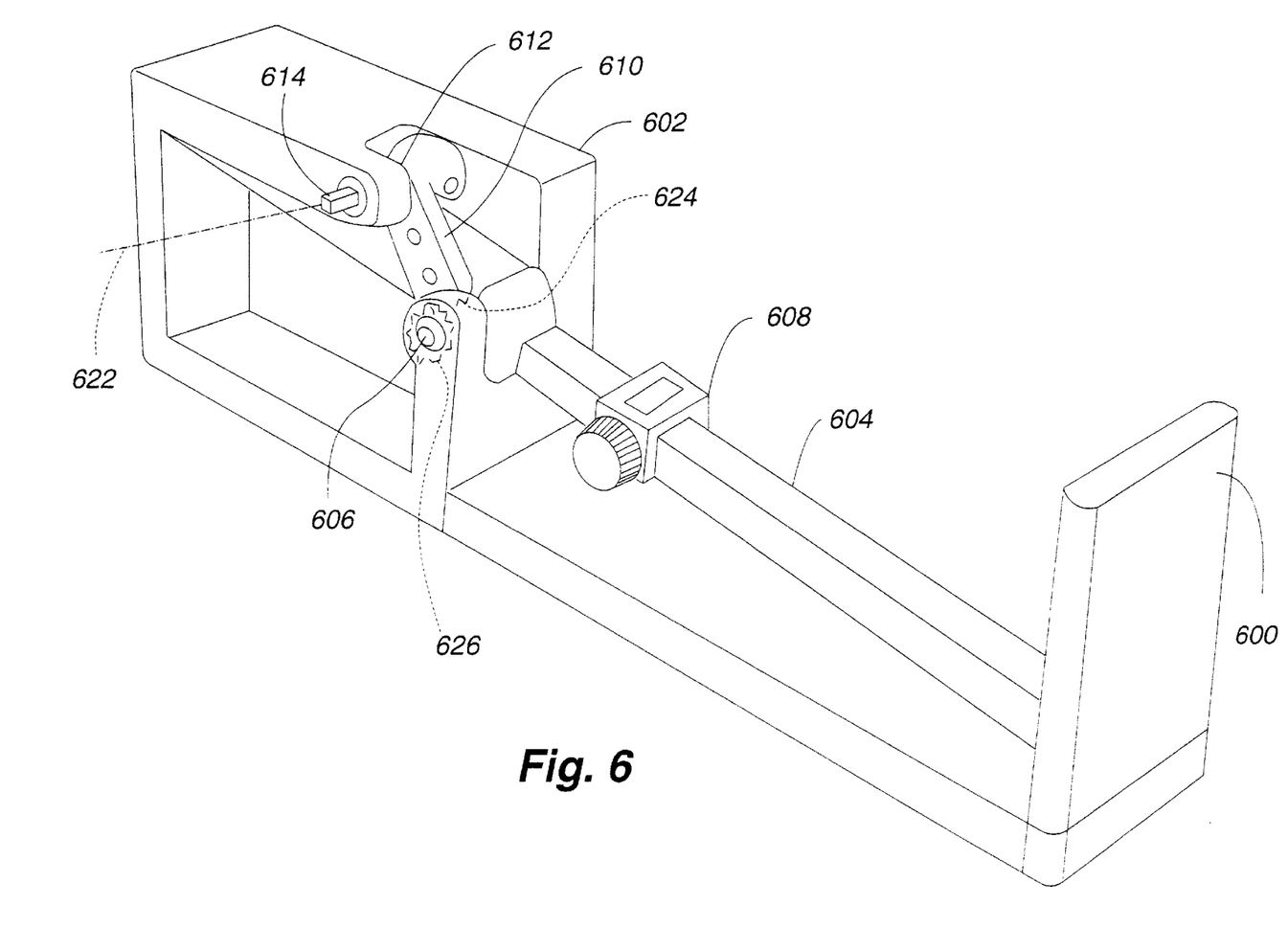
FIG. 6 is a prospective view of a torque setting-checking device according to an embodiment of the present invention.

Referring to FIG. 6, a calibration device 600 has a frame 602 to which a beam member 604 is pivotable with respect to the frame about a pivot point 606. A weight 608 is attached to and movable along the beam member 604, and may be positioned according to a scale marked in torque units, e.g. newton-centimeters. A rigid gear arm 610 pivotable about axis 622 intermeshes with a gear coupled to the beam 604 at pivot point 606. A post 614 is rigidly attached to arm 612 such that rotation of post 614 rotates arm 610 moving arm teeth 624, rotating gear 626 and pivoting attached beam 609, against the urging of weight 608. The amount of torque applied to post 614 which is sufficient to lift beam 604 depends on the linear position of weight 608. Since the torque is set by a gravity standard, it will be substantially non-variable and, in particular, will not degrade as a result of a change in a spring constant.

The torque wrench is calibrated to a non-variable standard by first setting weight 608 to a specific torque. Ratchet 506 is then fitted over post 614. The handle 514 is initially positioned with the lowest possible torque setting thus initially the torque wrench will slip and the beam 604 will not be lifted. Handle 514 is then rotated slightly to increase the torque setting of the wrench and the wrench is used to attempt to rotate the post 614 and lift the beam 608. If the torque setting to the wrench is too low to permit the torque wrench to rotate the post 614, the handle 514 is rotated further, to further increase the torque setting of the wrench and the wrench is again applied to the post 614. By repeating this process, the torque wrench is adjusted until the available maximum torque is just sufficient to rotate the post 614 and lift the beam 604, at which point the torque wrench has been adjusted to the torque indicate by the position of the weight 608 on the torque scale of the beam 604. The torque wrench is now calibrated to the torque setting selected and may be used, e.g. to fit the support device 200 into implant 100 by engaging and rotating the hexagonal outer surface 217 of the upper post member.

In use, after the practitioner has drilled and tapped an appropriate size recess in the patients jawbone 106 and inserted the implant 100, the practitioner selects a post among a plurality of available posts, having a desired color depth 211 (e.g. matching the thickness of the gum tissue 108) and a desired diameter 203, e.g. select to provide desired stability for the prosthesis 112, yet avoid disability of the color after the prosthesis is positioned. The practitioner then inserts the smooth portion 208 of the host 200 into the threaded well of the implant 100 thus achieving desired axial alignment of the post 200 with the axis of the implant 100 so that the post threads 206 are sufficiently axially aligned with the implant threads 102 to avoid cross threading. The post 200 is then rotated to engage the post threads 206 with the implant threads 102. Initial rotation may be by hand or with a wrench. In the final stages of insertion, it is desired to provided a predetermined amount of torque such as about 30 newton-centimeters. Preferably, the practitioner adjusts a torque wrench such as the wrench depicted in FIG. 5, using a calibration device such as the device of FIG. 6 to set the torque wrench at the desired maximum torque. The practitioner then couples a socket to the ratchet portion of the torque wrench and engages the socket with a wrench engaging surface of the post, such as one or more flat surfaces, e.g. surfaces 209. The practitioner then uses the wrench to rotate the post 200 to the desired torque with respect to the implant 100 drawing surface 210 tightly and in sealing relation to the top of the implant 104. The practitioner then aligns the thread of a healing cap (FIG. 3) with threads 217 on the top of the post and rotates the healing cap to engage the healing cap with a post 200 and seat the bottom surface 304 of the healing cap against the upper flange 214 of the post. If desired, a temporary tooth prosthesis may be cemented over the healing cap.

The practitioner will take an impression of the patient's mouth either before installing the healing cap or at a later time, after (possibly temporarily) removing the healing cap. The impression is used as described above and typically by a technician, in combination with a post analog device as a guide for pouring a prosthesis which will have an exterior and interior shape such that when mounted on the installed post the prosthesis will have the desired position and external shape. Because the installed post includes a flat portion or other wrench engaging surface, the analog device will contain a similar surface and thus when the analog device is used as a part of the mulled or form in which a cast is made, the hollow portion of the prosthetic tooth will contain a mating flat portion or wrench engaging surface. The mating relationship of the flat surface of the prosthetic and the flat surface of the installed post permits the practitioner to index the prosthetic tooth post in order to achieve the desired alignment when the prosthetic is installed.

Although it would be possible to produce a prosthesis without using an analog, it is believed that using the analog provides the advantage of establishing a nearly perfect margin for the prosthesis form as opposed to relying solely on an impression (without using an analog) which can have an imperfect margin, e.g. in regions where tissue has moved or fallen in.

After desired healing has occurred, the practitioner will remove the healing cap (and temporary prosthesis) if any and may, if desired, remove the tip 222 by breaking or cutting at the constriction 216. The prosthesis formed as described above is then cemented to the tapered portion 213 of the post and the procedure is complete. One prosthetic restorative procedure which can be used includes the following steps. A healing cap is placed onto the implant at the time of implant uncovering . A post is placed at the time of implant covering or upon removing a healing cap. The post is secured to the implant with a torque wrench and a post cover is threaded on or cemented on. An impression of the post is made. A post analog is placed into the impression, secured to the impression, and a model is poured. A crown is fabricated using the removable dye with post analog. The post cover thread is separated from the top of the post. The crown is tied on and cemented on the post using convention and bridge techniques. Among other advantages, the present invention permits fabrication of the crown using standard crown and bridge techniques and requires no special training for restorative dentistry. The invention requires little in the way of additional restorative instrumentation, provides for low costs for restorative components, allows the practitioner to use a normal dental laboratory for preparation of the crown or other components, requires only small or minimal restorative "chair" time, provides reliable predictable results, provides temporary coupled superstructures that result in a passive bit, achieves smooth contours and margins for better periodontal health and maintenance, provides cosmetically pleasing appearance for the patient and increases patient satisfaction.

In light of the above description, a number of advantages of the present invention can be seen. The risk of cross-threading or stripping the screw threads of either the implant or the post is reduced or eliminated. The practitioner is provided with the ability to choose among a variety of post collar shapes for receiving a dental prosthesis to accommodate both variations in vertical thickness of the gum tissue and various sizes of prosthesis. The ability to customize the support device increases the degree of fit and comfort of the prosthesis as well as minimizing the chance for bacterial infection and/or decay because of loose fit of the prosthesis.

Size can be selected to define an emergence profile which starts at the top of the implant device, and extends out into the surrounding tissue, thus prohibiting the tissue from growing over the top of the implant device and distorting the fit between the implant, post and prosthesis. The threaded top for the post, allows a temporary healing cap to be threaded to the post rather than cemented, and facilitates removal of the temporary cap and, if desired, re-installation. A wrench-engaging surface allows the post to be firmly and snugly fitted into the implant device by means of engaging a torque wrench set at a predetermined torque setting. The predetermined torque setting and its application to installation of the post are effected without rotation of the implant device or trauma to the surrounding bone and tissue. Preferably one or more surfaces of the post can be used for both a wrench engaging surface and an indexing surface. A replica or analogue of the support device allows the practitioner to fabricate a permanent prosthesis without dissembling the support device from the patient. A calibration device allows the practitioner to directly calibrate a torque wrench by using a non-variable weight standard. The calibration device does not rely on a spring-based scale, and thus avoids the usual problems associated with metal fatigue and change of the spring constant through time and use.

A number of variations and modifications of the invention can be used. The invention is not limited to periodontal applications, and may be used to implant and fashion prostheses and the like into other bones or tissue. The amount and degree of threading on the lower portion of the support device can be varied; deeper implants may require more threads on the support device. Also, variations in the middle collar portion of the support device, and particularly the shape and slope of the flange surfaces, may be varied to accommodate tissue thickness and prosthesis size. In one embodiment, the post is driven to the implant with a torque of between about 30 to 40 newton-centimeters. Although in the depicted configuration, the angle 207 is shown to be about 65 degrees, other angles can be used depending on the desired thickness 211 and diameter 203, such as angles between 10 and 90 degrees providing a screw-type attachment for coupling the healing cap is advantageous because it can be coupled in a quick efficient manner and avoids the potential for problems arising with the use of cement in the vicinity of an open wound. By providing a non-variable torque wrench calibration device, which is quick and simple to use, it becomes easier for the practitioner to calibrate the wrench with high frequency, such as for every procedure, or multiple time during a procedure to insure providing the proper torque by providing a slip-type torque wrench with adjustable torque, which is manually driven, the practitioner received a tactile feedback which can be useful in avoiding overdriving the post and of a type which is available for an electrically or otherwise automatically driven torque device. Preferably the torque wrench is adjusted without reliance on the spring-based scale such as a scale located on the torque wrench handle (or other portion of the torque wrench). Thus in one embodiment, the torque wrench contains no torque scale on the wrench itself. In another embodiment, an approximate torque scale may be provided for initial adjustment to a torque value close to the final desired torque value before final adjustment of the torque using a calibration device. Preferably, the torque wrench is adjusted to a torque of between about 28 and 34 newton-centimeters, more preferably about 30 to about 32 newton-centimeters. In the depicted embodiment, the post 200 establishes an emergence profile beginning immediately at the top of the implant 100. As depicted in FIG. 2, the diameter 203 of the collar region is located at the depicted embodiment at the margin of the crown 112. The post 200 can be provided with a variety of thread sizes and shoulder shapes, e.g. to accommodate or bypass shapes at the upper portion of the implant 100 such as external hexes and squares, internal hexes and squares, and octagons and similar implant drive devices. The cap is useful in keeping tissue 108 from collapsing in over the shoulder of the post. If desired, the cap can be relined with acrylic allowing it to be cemented on the post when a temporary crown is formed as part of the healing cap. By using the analog device, laboratory crown fabrication procedures can be followed without needing to remove the post from the mouth. The analog device fits into a flexible impression of the post in the mouth and provides a precise die on which a crown can be fabricated. Thus, a perfect impression of the margins of the shoulder in the mouth is not essential since the analog provides the technician with a perfect metal margin to work with. In one embodiment, collar is provided in a plurality of heights in increments e.g. of 1 mm so that region 211 may be a height of 1 mm, 2 mm, 3 mm, 4 mm, etc. The diameter 203 may be in a diameter preferably between about the outer diameter of the implant 100 and about 7 mm (or more). In one embodiment the lower portion diameter 232 is about i.95 mm, the lower portion height is about 2 mm, the upper root portion height 236 is about 3.7 mm, the lower flare angle is about 30 degrees, the upper bevel angle 209 is about 30 degrees, the constriction diameter 216 is about 0.63 mm, the top height 238 is about 1.6 mm, the top diameter is about 1.5 mm, the width of the post at the lightest portion of the taper region 242 is about 2.95 mm and at the top of the taper portion 244 is about 1.5 mm. In one embodiment, the height 306 of the healing cap is bout 3.6 mm and the diameter is selected to match the collar shoulder diameter 203. In one embodiment the lower portion 406 of the analog 400 is provided with knurled services 408 to assist in handling the device.

The tapered shape of the upper portion of the support device need not be tapered from the top of the post to the collar. It may be tapered only at one or more portions, e.g. to accommodate variations in the prosthesis and the degree of interconnectability required with surrounding teeth and/or prosthesis.

The emergence profile or surface may vary e.g according to whether the practitioner is dealing with front or back teeth.

What is claimed is:

1. A device for use in positioning and securing a dental prosthesis to an implant device positioned in a patient comprising:

a support member having a distal root portion with external screw threads engagable with said implant device, and a proximal post portion with an upper region of said post portion having external screw threads;

a weakened region between said upper region and the rest of the device.

2. A method of positioning and securing a dental prosthesis to an implant device positioned in a patient which method comprises:

providing a support member configured for receiving a prosthesis, having a distal root portion, a middle collar portion, and a proximal post portion with a top region and a constricted region between said top region and the remainder of said support device;

coupling the support member to the implant device, removing the top from the post, and installing the prosthesis on the support member.

3. The method of claim 2, wherein the middle collar portion of the support member is greater in cross-section than said implant device.

4. The method of claim 3 wherein said collar portion has a lower surface flaring outward from said root portion.

5. The method of claim 3 wherein said collar portion has an upper surface tapering in to said post portion.

6. The method of claim 2 wherein the post tapers to define decreasing cross-sectional area in a direction from the middle collar portion toward the top of the post portion.

7. The method of claim 6 wherein the angle of the post taper is between 4 and 10 degrees.

8. The method of claim 2 wherein the distal root portion has two external surface portions, the lower surface portion being unthreaded and the upper surface portion having external screw threads.

9. The of claim 2 wherein the support member has a wrench engaging surface.

10. The of claim 9 wherein the wrench-engaging surface is substantially hexagonal in cross-section.

11. A method as claimed in claim 2, further comprising:

installing the prosthesis on the support member so as to be aligned in a preferred alignment with respect to the wrench engaging surface.

12. A method as claimed in claim 2, further comprising:

attaching a temporary healing cap to the top of the support member, and removing the temporary healing cap following healing of the surrounding tissue.

13. The method of claim 12 wherein neither the temporary healing cap nor the prosthesis contacts the implant device.

14. The method of claim 12, wherein a temporary crown is attached to the temporary healing cap before removal of the temporary healing cap and preceding the installation of the prosthesis on the supporting member.

15. The method of claim 12, wherein the prosthesis is attached to the support member by cementation.

16. The method of claim 12, wherein the temporary healing cap is attached to the support member by means of external screw threads on the support member.

17. A device for use in positioning and securing a dental prosthesis to an implant device positioned in a patient, comprising:

a support member with a distal root portion, a middle collar portion and a post portion, the root portion having a substantially cylindrical shape and defining a longitudinal axis, the root portion further having an upper and a lower portion, the lower portion having a smooth external surface with a first diameter and the upper portion having external threads defining a second diameter greater than said first diameter, the middle collar portion having a greater cross-section than said implant device and having an upper surface and a lower portion, the lower portion flaring outward from said root portion with said lower portion defining first and second surfaces at first and second different angles with respect to said longitudinal axis, the upper portion tapering in to said post portion, said post portion with a top region, the post tapering to the top region at an angle of about 6 degrees from the middle collar portion, the post further having a wrench-engaging hexagonal outer surface, and the top region of said post having a constricted stem region for breaking an externally threaded top away from the rest of the post.

18. The device of claim 17 wherein the upper portion of said collar portion is angled so as to abut the prosthesis.

19. A method of constructing a dental prosthesis for installation on a support device attached to an implant device positioned in a patient which method comprises:

providing a support member with a wrench engaging surface, providing an adjustable torque wrench, setting the torque of said wrench using a non-variable standard, providing a calibration device having weight which can be moved to set the amount of torque needed to rotate a first post;

engaging the torque wrench with said first posts;

adjusting the torque of said adjustable torque wrench until rotation of the wrench causes rotation of said first post; and using said torque wrench to install said support member.

* * * * *

UNITED STATES PATENT AND TRADEMARK OFFICE
CERTIFICATE OF CORRECTION

PATENT NO. : 5,816,809
DATED : October 6, 1998
INVENTOR(S) : Sapkos

It is certified that error appears in the above-indentified patent and that said Letters Patent is hereby corrected as shown below:

column 1, line 5
    delete "1992" and replace with --1995--

Signed and Sealed this

Third Day of April, 2001

Attest:

NICHOLAS P. GODICI

*Attesting Officer*      *Acting Director of the United States Patent and Trademark Office*